United States Patent

Hansen

(10) Patent No.: US 8,585,652 B2
(45) Date of Patent: Nov. 19, 2013

(54) HAEMOSTATIC VALVE ASSEMBLY

(75) Inventor: Sebastian Hansen, Vordingborg (DK)

(73) Assignee: Cook Medical Technologies LLC, Bloomington, IN (US)

( * ) Notice: Subject to any disclaimer, the term of this patent is extended or adjusted under 35 U.S.C. 154(b) by 11 days.

(21) Appl. No.: 13/116,561

(22) Filed: May 26, 2011

(65) Prior Publication Data

US 2012/0109063 A1 May 3, 2012

(30) Foreign Application Priority Data

Nov. 3, 2010 (GB) .................................. 1018530.4

(51) Int. Cl.
*A61M 5/178* (2006.01)

(52) U.S. Cl.
USPC .................................................... 604/167.03

(58) Field of Classification Search
USPC ................ 604/167.03, 167.04, 246, 249, 256
See application file for complete search history.

(56) References Cited

U.S. PATENT DOCUMENTS

| | | |
|---|---|---|
| 4,673,393 A | 6/1987 | Suzuki et al. |
| 5,176,652 A | 1/1993 | Littrell |
| 5,391,154 A | 2/1995 | Young |
| 5,397,310 A | 3/1995 | Chu |
| 5,429,609 A | 7/1995 | Yoon |
| 5,514,109 A | 5/1996 | Mollenauer |
| 5,653,697 A | 8/1997 | Quiachon et al. |
| 5,722,958 A | 3/1998 | Gravener et al. |
| 5,782,817 A * | 7/1998 | Franzel et al. ................ 604/256 |
| 6,595,964 B2 * | 7/2003 | Finley et al. .................. 604/246 |
| 6,808,509 B1 | 10/2004 | Davey |
| 7,294,296 B2 | 11/2007 | Davey |
| 2005/0171479 A1 | 8/2005 | Hruska et al. |
| 2005/0228346 A1 * | 10/2005 | Goode et al. ............. 604/164.07 |
| 2008/0172003 A1 * | 7/2008 | Plishka et al. ................ 604/249 |

FOREIGN PATENT DOCUMENTS

| | | |
|---|---|---|
| EP | 0674879 | 10/1995 |
| EP | 0968026 B1 | 1/2000 |

OTHER PUBLICATIONS

PCT/US2011/038126 May 26, 2011 Cook Medical Technologies LLC International Search Report.
PCT/US2011/038126 May 26, 2011 Cook Medical Technologies LLC International Written Opinion.

* cited by examiner

*Primary Examiner* — Aarti B Berdichevsky
(74) *Attorney, Agent, or Firm* — Richard J. Godlewski

(57) ABSTRACT

A haemostatic valve assembly (18) is provided with a housing (24) having first and second ends (26, 28) within each of which there is provided an aperture of opening (30, 32). A flexible valve element (34) is disposed within the housing (24) between the first and second openings (30, 32). A mass of separate pellets (40) is located within the chamber (38) formed between the housing (24) and the valve element (34). The pellets (40) apply pressure to the valve element (34) so as to close the lumen (36) thereof. The pellets (40) are preferably made of a compressible material and such that when an element is inserted through the openings (30, 32) and thus through the valve assembly (18) the pellets (40) compress to allow opening of the lumen (36). The biasing force of the pellets (40) against the valve (34) provide constant sealing pressure to the valve assembly (18) without the need for any intervention by the clinician. The valve assembly is therefore entirely automatic.

20 Claims, 3 Drawing Sheets

HAEMOSTATIC VALVE ASSEMBLY

FIELD OF THE INVENTION

The present invention relates to a haemostatic valve assembly and to an introducer or deployment device incorporating such a valve assembly.

BACKGROUND OF THE INVENTION

There are well established techniques for carrying out endoluminal treatments and diagnoses on a patient. A diagnosis may, for example, involve injection of contrast material and saline solution. A treatment may, for example, involve insertion and deployment of implants or prostheses for carrying out surgical procedures. It may also or in the alternative involve insertion, use and removal of catheters or tools, such as angioplasty or moulding balloons. A treatment may also involve injection of contrast material, saline solution, administration of medicaments and so on. The treatments and diagnoses can be effected within a patient's vascular system, such as arteries or veins. They can also be carried out within other bodily tubes which carry pressurized fluids, examples being the bilary tree and urological system, as well as within other organs such as the cerebral ventricles and so on.

Endoluminal deployment or treatment devices typically include an elongate catheter assembly having an outer sheath which is inserted into the vasculature of the patient from a remote access point up to the deployment or treatment site. For example, for treatment in the aorta, the catheter assembly may be introduced from the femoral artery and fed through the patient's arteries until the distal end of the assembly is located at the position in the aorta at which the treatment is to be carried out. The outer sheath may be used for the passage and retention of elongate deployment elements, for instance catheters or pusher rods, as well as a medical device to be implanted into the patient. The sheath may also be used for carrying tools, catheters for administering medicaments and so on.

In the course of such treatments or endoluminal diagnosis it is important to ensure that the patient does not suffer unnecessary fluid loss through the sheath. For this purpose, it is known to provide at the proximal end of the introducer one or more haemostatic valves in series to close off leakage through the outer sheath. All other catheter based components which have the ability to allow fluid loss therethrough also require some form of sealing or valving.

Haemostatic valve assemblies must allow sliding movement of a variety of different delivery or treatment elements through the valve assembly, as thus through the sheath, while at the same time keeping a seal as such elements pass through or are located in the valve assembly. They must also seal when there is no element in the assembly, that is when the sheath is empty. This requirement generally presents a compromise in terms of sealing efficiency and friction imparted upon any device inserted into the valve assembly. For this reason, some valves provide manual opening and closing of the valve. This, however, involves at least one additional step in the medical procedure and can also lead to the valve failing to provide a seal when in the open configuration, therefore requiring additional valving to avoid unnecessary bodily fluid loss during operation of the valve.

Examples of earlier valves can be found, for instance, in U.S. Pat. Nos. 4,673,393, 5,176,652, US-A-2005/017,479, U.S. Pat. Nos. 5,391,154 and 5,653,697.

SUMMARY OF THE INVENTION

The present invention seeks to provide an improved haemostatic valve assembly and an improved intraluminal treatment or deployment device.

According to an aspect of the present invention, there is provided a haemostatic valve assembly for an introducer, including a housing provided with first and second ends, each of the first and second ends including an opening, the openings providing for the passage of a device through the valve assembly; at least one flexible valve element disposed in the housing, the valve element including a lumen extending between the openings of the first and second ends, the lumen being openable for the passage of a device therethrough and closable to seal the valve assembly, the housing and valve element forming a valve chamber therebetween; and a volume of pellets within the valve chamber, the pellets providing a biasing force on the valve element in a lumen closing configuration.

This arrangement of haemostatic valve assembly provides a mechanism by which the valve element is continuously biased into a sealing condition in all operating states. More specifically, the pellets, which are preferably separate from one another and freely movable within the valve chamber, will be displaced by any opening of the lumen, for instance when a catheter is inserted into the valve, but will always tend to move into a configuration in which they close the valve element, as a result of resiliency in the structure. There is thus no need, in the preferred embodiment, for any manual intervention by the clinician. In other words, in the preferred embodiment it is not necessary to provide any other sealing mechanism or device as the assembly works automatically.

Advantageously, the flexible valve element extends around the entire circumference of the lumen. In other embodiments, the lumen could be formed in part from the flexible valve element and in another part by a non-flexible wall of the valve structure.

Preferably, the flexible valve element extends across the entirety of a space between the openings. The structure will work with a valve element which extends across only a part of the distance between the ends of the housing. For instance, a part of this space could be taken up with a wall or support structure extending from the housing end towards the middle of the housing and which provides no valving function but which simply supports a shorter valve element. It is preferred, however, that the flexible valve element extends across the entirety of the distance between the two ends of the housing as this would provide a greater length of sealing function, which can substantially increase the efficiency and sealing characteristics of the valve compared to a valve which seals over only a shorter distance.

In the preferred embodiment the pellets are substantially spherical. This shape ensures smoothest movement and sliding of the pellets with respect to one another. Other shaped pellets are, however, not excluded. The pellets could, for example, be oval, rod-shaped, irregularly shaped or of any other shape which allows them to move and slide with respect to one another.

The pellets are biased towards the valve element, that is towards the axial centre of the housing, by resiliency and/or elasticity within the assembly. As described herein, this resiliency can be provided by one or more of a variety of different characteristics to the pellets, housing, valve element and the like.

It is preferred that the pellets are formed of a compressible or compliant material, advantageously an elastomeric material such as at least one of rubber, a rubber-like material, silicon, a foam. The use of compliant pellets enables these to deform, typically to compress, when they are subjected to a compression force, for instance when an element is introduced into the valve. This compliance ensures that the pellets impart on the valve element and in particular on the lumen of the valve element a constant sealing force. It is not, however, necessary for the pellets to be made of a compressible material. For instance, the housing could be made at least partially of a compliant or elastomeric material to allow for movement of the pellets and to provide for the necessary restoring or biasing force to the valve assembly. In other embodiments, the valve element can provide the necessary compliancy of the structure to allow movement of rigid pellets as an element is introduced into the valve assembly.

It is envisaged that the valve assembly could include pellets formed of different materials and in particular of different characteristics, for instance to have a proportion of rigid pellets and a proportion of compressible pellets.

It is considered that pellets having an average diameter from 1 millimeter to 10 millimeters are particularly suitable, preferably from 2 to 5 millimeters. The pellets do not need to be of the same diameter, although this is preferred.

The valve element may be made of a compliant material or of a low compliance material. In some embodiments it may be desired that the valve element is coated with a lubricious coating on the luminal side thereof.

According to another aspect of the present invention, there is provided an introducer assembly including a sheath having a distal end and a proximal end; a haemostatic valve assembly coupled to the proximal end of the sheath; the haemostatic valve assembly including a housing provided with first and second ends, each of the first and second ends including an opening, the openings providing for the passage of a device through the valve assembly; at least one flexible valve element disposed in the housing, the valve element including a lumen extending between the openings of the first and second ends, the lumen being openable for the passage of a device therethrough and closable to seal the valve assembly, the housing and valve element forming a valve chamber therebetween; and a volume of pellets within the valve chamber, the pellets providing a biasing force on the valve element in a lumen closing configuration.

DESCRIPTION OF THE DRAWINGS

Embodiments of the present invention are described below, by way of example only, with reference to the accompanying drawings, in which.

DESCRIPTION OF THE PREFERRED EMBODIMENT

Figure 1:
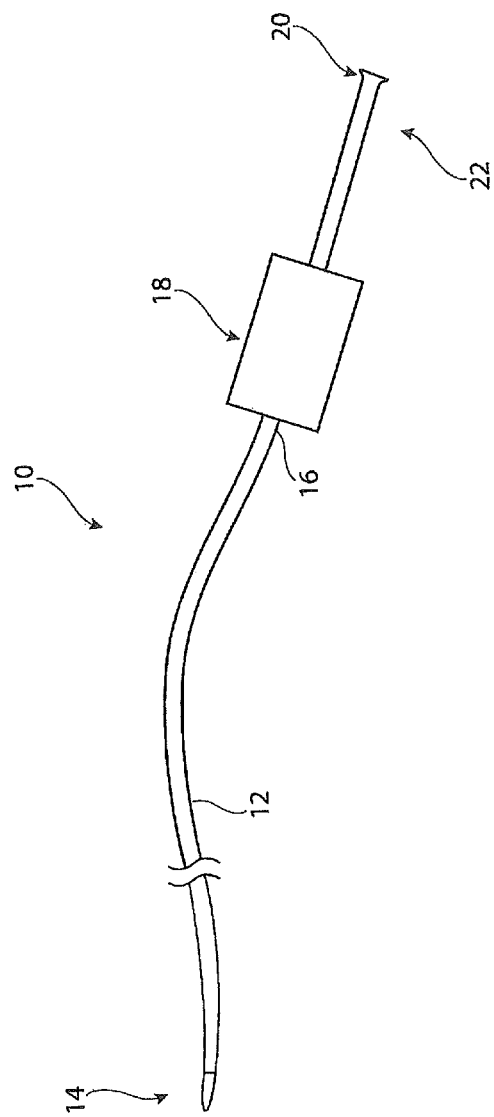
FIG. 1 shows in schematic form a perspective view of an example of introducer provided with a haemostatic valve assembly according to an embodiment of the present invention.

Referring to FIG. 1 there is shown an example of introducer assembly 10, having a general form which is conventional in the art but which is provided with a haemostatic assembly as taught herein. The introducer assembly 10 may be used for the endoluminal implantation in a patient of medical devices such as stents, stent grafts, vena cava filters, occluders and other such devices. The introducer 10 may also be used for the deployment of any other medical treatment and/or diagnostic tools.

The introducer assembly 10 includes, as it typical, a sheath 12 designed to be fed through the vasculature of a patient. The sheath 12 has a distal end 14 which in use is positioned at the treatment site, and a proximal end 16 coupled to a haemostatic valve assembly 18 and which remains outside the patient during the procedure. A cannula or catheter element 20 extends from the haemostatic valve assembly 18 at a proximal end 22 of the introducer 10. The sheath 12, cannula 20 and haemostatic valve assembly 18 have aligned lumens therein for the passage of elements into the sheath from the proximal end 22 of the introducer.

The sheath 12 is used as a cover and guide for components positioned within the introducer 10, be they medical device carrier elements, tools and the so on. Typically, the sheath 12 is first placed within the patient, for instance by means of the Seldinger technique, and then left in position while the medical procedure is effected. In many procedures it is necessary to insert into and remove different components from within the sheath (through the proximal cannula 20), while in other cases the sheath 12 may be preloaded with an element such as a medical device and carrier assembly.

It will be appreciated that the introducer assembly 10 will typically also include various ports for flushing fluid and for medicaments, for instance, as well as other components associated with the deployment of medical devices or treatment tools. These are not shown in the drawings as they are commonplace and not required for an understanding of the teachings herein.

The haemostatic valve assembly 18 provides suitable valving and sealing of the sheath 12, in this example, to ensure that no bodily fluid is unnecessarily lost during the procedure. The valve assembly 18 must thus provide a sealing function both when an element or tool is located in the sheath (and through the valve 18), as well as when the sheath 12 is empty, that is it does not carry any component therewithin. In this regard, the valve assembly 18 must be able to seal also around elements of different sizes, for instance different catheters, guide wires, push rods and other elements.

Figure 2:
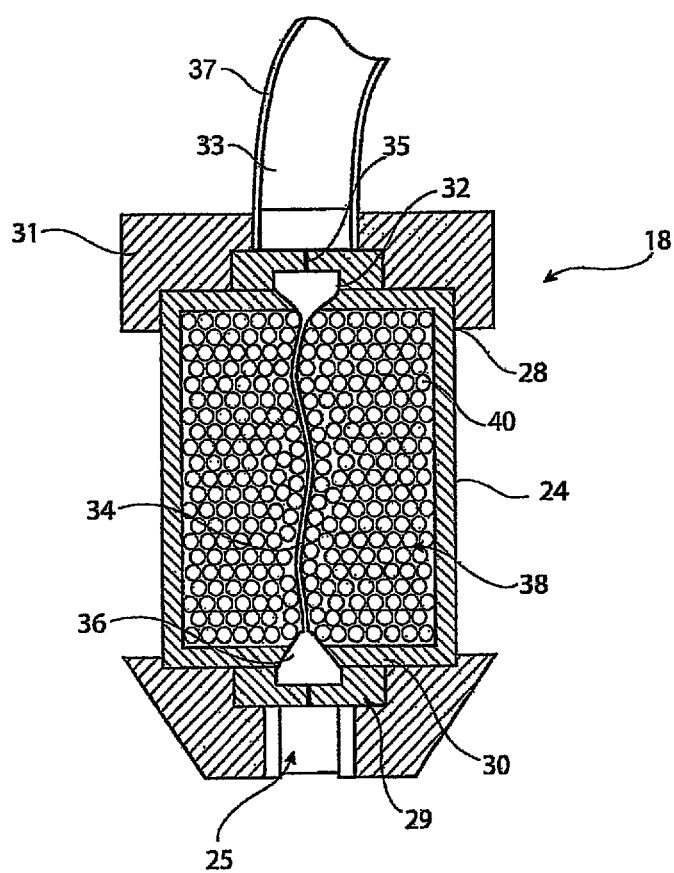
FIG. 2 is a longitudinal cross-sectional view of a preferred embodiment of valve assembly.

Referring now to FIG. 2, there is shown a preferred embodiment of haemostatic valve assembly 18 for use with the introducer 10 of FIG. 1. It is to be understood that valve assembly 18 could be used with other forms of introducer or deployment assembly other than that shown in FIG. 1.

The haemostatic valve assembly 18 includes a housing 24 which in this example is a generally circular cylinder. The housing 24 includes a first, distal, end 26 and a second, proximal, end 28. In this example, the ends 26 and 28 are walls of the case forming the housing element 24. The distal end 26 is provided with a first opening 30, while a second opening 32 is provided in the proximal end 28. These openings 30, 32 are sized to provide for the passage of catheters and other elements through the valve assembly 18 and are preferably round, although could have other shapes.

Coupled to the distal wall 26 of the housing 24 is a distal cap 25 which tapers in a distal direction and which is provided with a bore 27 aligned with the first opening 30 and at least as large as this in diameter. The bore 27 may be lined with a low friction coating or tubing as shown. Located in a recess in the cap 25, in this embodiment, there is provided a disk valve 29 which provides additional sealing. In many embodiments it is not necessary to have valve 29.

Coupled to the proximal wall 28 of the housing 24 is a proximal cap 31 which is provided with a bore 33 aligned with the second opening 32 and at least as large as this in diameter. The bore 33 may be lined with a low friction tubing 37 as shown. Located in a recess in the proximal cap 31, in this embodiment, there is provided a disk valve 35 which provides additional sealing. In many embodiments it is not necessary to have valve 35. The first end 26 of the valve assembly 18 is in this embodiment coupled to the sheath 12, whereas the second end 28 is coupled to the tube 37, which may be the cannula 22. The internal lumens of the sheath 12 and tube 37 thus couple to the openings 30, 32, respectively. The couplings are fluid tight.

Disposed within the housing member 24 is a flexible valve element 34, which in this embodiment is attached to the internal surfaces of the end walls 26 and 28. The valve element 34 includes a lumen 36 which couples the first and second openings 30, 32 to one another. The lumen 36 allows for the passage of a catheter or other elongate element through the valve assembly 18.

In this embodiment, the valve element 34 is in the form of a tube of flexible material the ends of which are secured, by bonding, welding or other fixing, to the internal surfaces of the end walls 26, 28 so as to surround of the apertures 30, 32. The lumen 36 of the valve element 34 may have a diameter which is larger than the diameter of the openings 30, 32 and is preferably round in transverse cross-section, although this is not necessary. As can be seen in FIG. 2 in particular, in the preferred embodiment the valve element 24 has a non-stretched diameter which is substantially less than the diameter of the openings 30, 32, for which there are provided at the ends of the element 34 generally frusto-conical end portions as shown. The end portions could be formed as part of the valve element 34 or could be of a different material and fixed to the tubing of the valve element 34.

In the preferred embodiment, the valve element 34 is formed of a compliant material, although it could equally be made of a substantially non-compliant material).

The valve element 34 forms with the housing 24 a valve chamber 38. In this embodiment, the valve chamber 38 is annular, having circular inner and outer walls (formed by the outer surface of the valve element 34 and the inner surface of the housing 24 respectively).

Disposed within the chamber 38 is a volume or mass of pellets 40. In the preferred embodiment the pellets 40 are packed within the chamber 38 so that they provide a constant biasing force against the valve element 34, even when there is no element located in the valve assembly 18, that is in the lumen 36 of the valve element 34.

In the preferred embodiment, the pellets 40 are substantially spherical and formed of a compressible, compliant and/or elastomeric material, for instance rubber, a rubber-like material, silicon or a foam. In some embodiments, it is envisaged that the pellets 40 can be made of different materials, for instance with a proportion of the pellets being compressible and another proportion being rigid or relatively non-compliant.

It has been found that pellets having an average diameter from 1 millimeter to 10 millimeters provides good sealing performance, preferably from 2 to 5 millimeters.

The valve element 34 may be provided on its internal surface (that is, the surface forming the lumen 36) with a lubricious coating. Such a coating will facilitate the reciprocal movement of devices into and out of the valve assembly 18 and can improved the quality of the seal. Such a coating may not be necessary in cases where the valve element is formed of a relatively low friction material.

It will be appreciated that the pellets 40, when packed within the chamber 38, will apply a biasing pressure against the leaflet or leaflets of the valve element 34, which will bias the lumen 36 towards a closed configuration. Given the nature of the separate pellets 40, this biasing pressure will be non-uniform along the length of the valve element 34 and also circumferentially around the valve element. As a result, the valve element 34 and the lumen 36, will not close in an entirely linear manner from the opening 30 to the opening 32 but will do so unevenly, as can be seen in FIG. 2. That is, the wall(s) of the valve element 34 will be pressed together at different pressures along its length and around its circumference to give the lumen a somewhat uneven or undulating form from one end 26 to the other end 28 of the valve assembly 18. This provides an improved seal, with the result that it is not necessary to create a large sealing pressure, thus reducing the operating friction of the valve assembly 18 and therefore facilitating the insertion and removal of elements through the assembly 18.

Because the lumen 36 extends from the first opening 30 of the housing 24 to the second opening 32 of the housing 24 along an undulating path, the distance the lumen 36 traverses is longer than the distance of a straight path between the same openings 30, 32 of the housing 24. Thus, where the lumen 36 takes a somewhat uneven or undulating form, as in FIG. 2, the total length of the undulating lumen 36 will be greater than the length of the housing 24, as measured along its longitudinal axis.

With a housing 24 which is circularly cylindrical as in the preferred embodiment, there is produced an overall compression force against the valve element 34 which is generally even in all radial directions and similarly a generally even increase in this force on radial expansion of the lumen 36, which occurs during the insertion of a circular cylindrical element through the valve. This ensures that the lumen 36 will be generally evenly biased to a sealing condition. It is to be understood that the overall pressure applied generally by the mass of pellets 40 is subject to the small variations caused by the size and shape of the pellets themselves, which could be said to provide a non-linear "fine" closing of the lumen 36.

Figure 3:
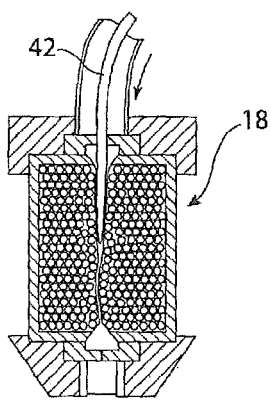
FIGS. 3 to 5 show the valve assembly of FIG. 2 in different operating states.
Figure 4:
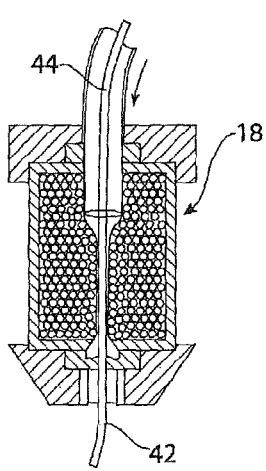
Figure 5:
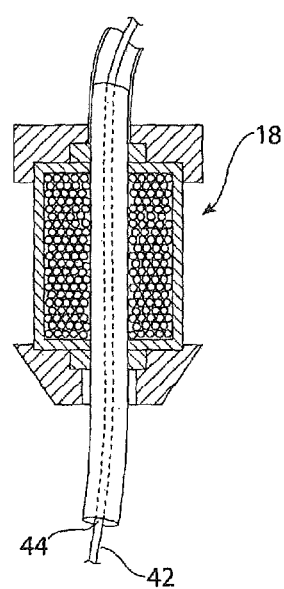

In use as can be seen in FIGS. 3 to 5, a device, such as a guide wire 42 can be fed into the valve element first. FIG. 3 shows the guide wire 42 being fed from the proximal end of the assembly 18 through the valve element, in conventional manner. In the preferred embodiment, as shown in FIG. 3, the valve element 34 is sufficiently flexible to be able to remain substantially closed in that part which has not been opened by the guide wire 42 as well as to seal around the guide wire 42. This ensures that a substantial length/depth of sealing is maintained by the sealing element 34 at all times. The guide wire 42, as with any other element such as a catheter, pusher element or the like, need only be inserted into the valve assembly 18, without any other intervention being required by the clinician. When a device is so inserted into the assembly 18, the pellets 40 will move relative to one another and compress as the device is passed through the valve 34. Specifically, the device will push the leaflet or leaflets of the valve element 34 so as to open the lumen 36 and move and compress at least some of the pellets 40. The pellets 40 will continue to impart a closing bias to the valve leaflet 34, thereby to ensure that the valve assembly 18 continues to provide a seal.

Devices of different sizes will open the valve 34 by different amounts and will thus move and compress the pellets 40 to different extents. Larger devices fed through the valve assembly 18 will cause greater displacement and/or compression of the pellets 40 compared to devices of smaller diameter. Thus, the valve assembly 18 can accommodate a variety of sizes of inserts/devices therethrough, typically up to the size of the openings 30, 32.

An example is shown in FIGS. 4 and 5, in which a catheter 44 is fed into and through the valve assembly 18 from its proximal end first. As can be seen, the catheter 44, which in this embodiment has an outer diameter substantially the same as the inner diameter of the openings 30, 32, opens the valve element 34 against the force of the pellets 40 and in some embodiments also to stretch the material of the valve element 34. Again, the valve element 34 is sufficiently compliant in the preferred embodiment to close around those portions thereof which have not been opened by the catheter 44 as well as around the catheter 44.

When an element is fed through the valve assembly 18, such as the guide wire 42, catheter 44 or other element, the disk valves 29, 35, where provided, will also open. These, as is known in the art, may have a slit or aperture which allows them to open.

As explained with respect to the preferred embodiments, using a material for the valve leaflet or leaflets of the valve element 34 which is sufficiently conformable that during insertion of a device through the valve assembly 18, ensures that the lumen 36 will remain closed along those portions of the valve 34 yet to be opened by the device being inserted into the valve assembly 18. The valve assembly will thus maintain a seal along substantially the entirety of its length, which ensures a good and effective seal in all operating conditions of the valve assembly 18.

The arrangement of FIGS. 2 to 5 also provides another advantage over many existing types of haemostatic valve, namely that the assembly 18 provides a seal which extends over a substantial distance, in the preferred embodiment sealing along substantially the entirety of the lumen 36. Sealing along a greater distance provides a better quality of seal and thus enables the use of a lower sealing pressure for similar or better sealing characteristics. This reduces the resistance on any device inserted into the valve assembly 18 and thus reduces the risk of kinking or other damage to that device as it is being inserted into or removed from the valve assembly 18. This is particularly advantageous with devices which are relatively delicate, such as guide wires, narrow diameter catheters and so on.

When it is desired to remove a device from the introducer assembly 10, the device can simply be pulled back, that is in a proximal direction. Once the distal end of the device reaches the valve assembly 18, and is pulled therethrough, the pellets 40 will move so as to close off that part of the lumen 36 which is no longer supported by the device being withdrawn. Once the device has been completely withdrawn from the valve assembly 18, and from the introducer assembly 10, the pellets 40 will rearrange themselves, generally substantially evenly, within the chamber 38 so as to close substantially the entirety of the lumen 36. Thus, the valve assembly 18 provides substantially constant sealing in all its operating conditions without the need for any manual intervention by the clinician. The valve works, thus, entirely automatically.

Of course, the direction of insertion or withdrawal of a device from the valve assembly is not important as the valve 34 will operate equally in both directions.

The above embodiment makes use of pellets 40 which are made of a compressible material. In another embodiment, all of the pellets 40 can be made of a non-compressible or substantially non-compressible material, with a biasing elasticity provided, for example, by using a compliant material for at least a part of the housing 24. In such an example, insertion of a device into the valve assembly 18 would cause some of the pellets to move into the compliant part of the housing 24 and thus to stretch this, generating a return force which biases the valve 34 closed by transmission of this force through the pellets 40. In another embodiment, the pellets and the housing could be made of non-compliant materials, with the valve element 34 providing the necessary stretching and return elasticity. For instance, the valve element 34 could be formed in a waisted configuration and such that when the pellets 40 move as a result of an insertion of a device into the valve assembly 18, the material of the valve element 34 stretches to accommodate the movement of the pellets 40.

The housing 24 need not be of a round-cross section and also need not be generally cylindrical as shown in FIG. 2. The assembly could, for example, be cuboidal or have any other desired shape. Such a shape could be determined, for example, on the basis of user preferences and also, for example, to accommodate other components of the introducer assembly 10 with a common manipulation or handle unit.

In the embodiment shown in FIGS. 2 to 5, the valve element 34 extends the entire distance from the ends or walls 26, 28 of the housing 24. It is envisaged in other embodiments that the valve element 34 could extend only part of this distance, with the remaining part being taken up by a valve support. Such a valve support could, for example, be a substantially rigid tube coupled to a respective end 26, 28 or could have any other structure. Similarly, it is not necessary for the valve element 34 to extend around the entire circumferential extent of the lumen 36. The valve element 34 could, for example, extend only partially around the circumference of the lumen 38 with the remainder being formed of a rigid wall or other support. Similarly, the valve element 34 need not be circular in transverse cross-section; in some embodiments it could have other forms.

The embodiments taught herein can provide a much enhanced sealing function compared to prior art haemostatic valves. Furthermore, as a result of the disclosed structure, the valve element does not have to be made from a compliant material as with existing haemostatic valves. The valve element could equally be made from a relatively non-compliant material, such as a material commonly used for endovascular balloons, for example polyethylene terephathalate (PET), polyethylene, nylon, PVC, or any other known materials. An advantage of non-compliant materials of this type is that they can be very flexible and have lower coefficients of friction compared to compliant materials.

What is claimed is:

1. A haemostatic valve assembly for an introducer, including a housing provided with first and second ends, each of the first and second ends including an opening, the openings providing for the passage of a device through the valve assembly; at least one flexible valve element disposed in the housing, the valve element including a lumen having an undulating form and extending between the openings of the first and second ends, the lumen being openable for the passage of a device therethrough and closable to seal the valve assembly, the closed lumen having an undulating form from the first end to the second end, the total length of the undulating lumen being greater than the length of the housing as measured along the longitudinal axis, the housing and the valve element forming a valve chamber therebetween, the valve chamber having a wall at least partly comprised of the housing; and a volume of pellets within the valve chamber, the pellets providing a biasing force on the valve element in a lumen closing configuration.

2. A haemostatic valve assembly according to claim 1, wherein the flexible valve element extends around an entire circumference of the lumen.

3. A haemostatic valve assembly according to claim 1, wherein the valve chamber extends circumferentially around the lumen.

4. A haemostatic valve assembly according to claim 1, wherein the openings in the first and second ends of the housing are separated by a distance, the flexible valve element extending across substantially the entirety of said distance.

5. A haemostatic valve assembly according to claim 1, wherein the pellets are substantially spherical.

6. A haemostatic valve assembly according to claim 1, wherein the pellets have an average diameter from 1 to 10 millimeters.

7. A haemostatic valve assembly according to claim 1, wherein the pellets have an average diameter from 2 to 5 millimeters.

8. A haemostatic valve assembly according to claim 1, wherein the valve element is formed of a compliant material.

9. A haemostatic valve assembly according to claim 1, wherein the valve element is formed of a low compliance material.

10. A haemostatic valve assembly according to claim 1, wherein the valve element is coated with a lubricious coating on the lumen side thereof.

11. A haemostatic valve assembly according to claim 1, wherein the pellets fill the entirety of the chamber when the lumen is closed.

12. A haemostatic valve assembly according to claim 1, wherein the pellets are formed of a compressible or compliant material.

13. A haemostatic valve assembly according to claim 12, including pellets formed of different materials.

14. A haemostatic valve assembly according to claim 12, wherein the pellets are formed of an elastomeric material.

15. A haemostatic valve assembly according to claim 14, wherein the pellets are formed of at least one of rubber, a rubber-like material, silicon and a foam.

16. A haemostatic valve assembly for an introducer, including a housing provided with first and second ends, each of the first and second ends including an opening, the openings providing for the passage of a device through the valve assembly; at least one flexible valve element disposed in the housing, the valve element including a lumen having an undulating form and extending between the openings of the first and second ends, the lumen being completely enclosed around its circumference and longitudinal length and coupling the first and second openings to one another, the lumen being openable for the passage of a device therethrough and closable to seal the valve assembly, the closed lumen having an undulating form from the first end to the second end, the total length of the undulating lumen being greater than the length of the housing as measured along the longitudinal axis, the housing and the valve element forming a valve chamber therebetween, the valve chamber having a wall at least partly comprised of the housing; and a volume of pellets within the valve chamber, the pellets providing a biasing force on said valve element in a lumen sealing configuration.

17. A haemostatic valve assembly for an introducer according to claim 16, wherein the pellets fill the entirety of the chamber when the lumen is closed; and the flexible valve element is a tube of material, the ends of which are secured to the internal surfaces of the first and second ends of the housing so as to surround the openings of the housing.

18. A haemostatic valve assembly for an introducer according to claim 17, wherein the flexible valve element extends across only a part of a distance between the ends of the housing, and part of the distance between the ends of the housing is taken up with a wall or support structure extending from the housing end towards a middle of the housing the lumen is completely enclosed in part by the flexible valve element and in part by a support structure extending from the housing end towards the middle of the housing.

19. An introducer assembly including a sheath having a distal end and a proximal end; a haemostatic valve assembly coupled to the proximal end of the sheath; the haemostatic valve assembly including a housing provided with first and second ends, each of the first and second ends including an opening, the openings providing for the passage of a device through the valve assembly; at least one flexible valve element disposed in the housing, the valve element including a lumen having an undulating form and extending between the openings of the first and second ends, the lumen being openable for the passage of a device therethrough and closable to seal the valve assembly, the closed lumen having an undulating form from the first end to the second end, the total length of the undulating lumen being greater than the length of the housing as measured along the longitudinal axis, the housing and the valve element forming a valve chamber therebetween, the valve chamber having a wall at least partly comprised of the housing; and a volume of pellets within the valve chamber, the pellets providing a biasing force on the valve element in a lumen closing configuration.

20. A haemostatic valve assembly according to claim 19, wherein the pellets fill the entirety of the chamber when the lumen is closed.

* * * * *